United States Patent
Kelly et al.

(10) Patent No.: US 6,239,126 B1
(45) Date of Patent: May 29, 2001

(54) ARYLPIPERIDINE AND ARYL-1,2,5,6-TETRA-HYDROPYRIDINE UREA DERIVATIVES

(75) Inventors: Michael G. Kelly, Newbury Park, CA (US); Gan Zhang, Plainsboro, NJ (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/459,791

(22) Filed: Dec. 13, 1999

Related U.S. Application Data

(60) Provisional application No. 60/150,700, filed on Dec. 17, 1998.

(51) Int. Cl.⁷ .................. A01N 43/00; A01N 31/538; C07D 211/26; C07D 211/18; C07D 401/00
(52) U.S. Cl. .................. 514/211; 514/212; 514/218; 514/235.5; 514/255; 514/307; 514/314; 514/318; 514/326; 514/330; 514/331; 540/481; 540/544; 540/553; 544/130; 544/360; 546/146; 546/169; 546/193; 546/194; 546/208; 546/209; 546/210; 546/231; 546/232
(58) Field of Search .................. 546/231, 232, 546/193, 194, 208, 209, 210, 169, 146; 540/481, 544, 553; 544/130, 360; 514/211, 212, 218, 235.5, 255, 307, 314, 318, 326, 330, 331

(56) References Cited

U.S. PATENT DOCUMENTS

| | | | |
|---|---|---|---|
| 4,071,524 | * 1/1978 | Banitt | 260/293.77 |
| 4,797,489 | 1/1989 | Abou-Gharbia et al. | 544/295 |
| 4,882,432 | 11/1989 | Abou-Gharbia et al. | 544/331 |
| 5,364,864 | * 11/1994 | Bigg et al. | 514/318 |

FOREIGN PATENT DOCUMENTS

| | | |
|---|---|---|
| 466585 | 7/1991 | (EP) . |
| 0661266 | 7/1995 | (EP) . |
| WO 9502592 | 1/1995 | (WO) . |
| WO 9504042 | 2/1995 | (WO) . |
| WO 9740038 | 10/1997 | (WO) . |

* cited by examiner

*Primary Examiner*—Alan L. Rotman
*Assistant Examiner*—Raymond Covington
(74) *Attorney, Agent, or Firm*—Rebecca R. Barrett

(57) ABSTRACT

Compounds of the formula

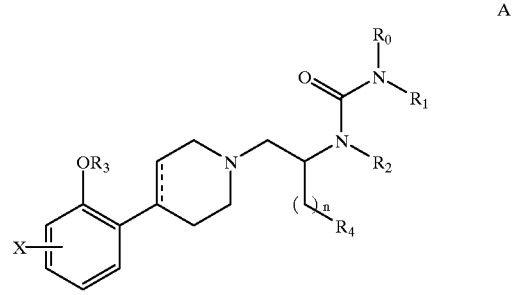

are useful for the treatment of disorder of the central nervous system including anxiety, depression, panic, alcohol and drug addiction, sexual dysfunction, sleep disorders, migraine, obesity, cognitive disorders and neurodegenerative diseases.

21 Claims, No Drawings

ARYLPIPERIDINE AND ARYL-1,2,5,6-TETRA-HYDROPYRIDINE UREA DERIVATIVES

This application claims the benefit of U.S. Provisional Application No. 60/150,700, filed Dec. 17, 1998.

BACKGROUND OF THE INVENTION

U.S. Pat. No. 4,882,432 teaches adamantyl and noradamantyl piperazine carbarnates and ureas with high 5-HT1A receptor affinities. These compounds, as well as those disclosed in U.S. Pat. No. 4,797,489 are useful for the treatment of CNS disorders.

EP 661266-A1 describes piperidino and piperazino 5-HT2 receptor antagonists and blood platelet aggregation inhibitors.

WO 9504042 describes 4-phenyl-4-phenylpropyl(enyl) piperidine tachykinin antagonists for treating pain or inflammation or emesis.

DESCRIPTION OF THE INVENTION

This invention relates to novel arylpiperidine urea and aryl-1,2,5,6-tetrahydropyridine urea derivatives. In accordance with this invention are provided novel arylpiperidine urea and aryl-1,2,5,6 tetrahydropyridine urea derivatives which are antagonists of the 5HT1A receptor subtype. By virtue of their high binding affinity to the 5HT1A receptor, compounds of the present invention are useful for the treatment of central nervous system (CNS) disorders such as depression, anxiety, panic, obsessive-compulsive disorder (OCD), sleep disorders, sexual dysfunction, alcohol and drug addiction, cognition enhancement, Alzheimer's disease, Parkinson's disease, obesity and migraine.

Compounds of the present invention are represented by the general formula (A),

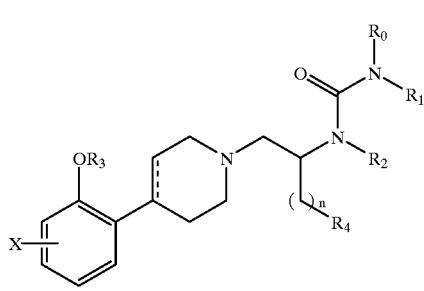

A in which:
- R0 and R1 are independently hydrogen, alkyl, cycloalkyl, heterocycloalkyl alkylcycloalkyl, alkylheterocycloalkyl, aryl or heteroaryl, or taken together R0 and R1 form a heterocycloalkyl, provided that R0 and R1 are not both hydrogen;
- R2 is hydrogen, alkyl or CH$_2$(R$_5$);
- R3 is hydrogen or alkyl;
- R4 is aryl or heteroaryl;
- R5 is alkyl, alkenyl or alkynyl;
- X is hydrogen, halogen, perhaloalkyl, hydroxy, alkoxy, perhaloalkoxy; n is an integer from 1 to 3; and the dotted line is an optional double bond, or a pharmaceutical salt thereof.

X is preferably halogen substituted at positions 4- or 5-, more preferably is 4-fluoro or 5-fluoro and most preferably is 5-fluoro-.

When R2 is an alkyl group, R2 is preferably a straight chain alkyl of 1 to 5 carbon atoms. R3 is preferably a straight chain alkyl of 1 to 4 carbon atoms.

In some preferred embodiments of the present invention, R0 and R1 are independently hydrogen or cycloalkyl or taken together are cycloalkyl or heterocycloalkyl. More preferably R0 and R1 are independently hydrogen or cyclohexyl or taken together are morpholino.

In still more preferred embodiments of the present invention, R0 and R1 are independently hydrogen or cyclohexyl, or taken together are morpholino, X is 5-fluoro, and R4 is phenyl.

"Alkyl" as used herein means a branched or straight chain having from 1 to 6 carbon atoms and more preferably from 1 to 5 carbon atoms. Exemplary alkyl groups include methyl, ethyl, propyl, isopropyl, butyl, isobutyl, t-butyl, pentyl and hexyl.

"Alkenyl" as used herein means a branched or straight chain alkyl having from 2 to 6 carbon atoms. Exemplary alkenyl groups include ethylene and propylene. In some embodiments of the present invention the alkenyl group may be substituted.

"Alkynyl" as used herein means a branched or straight chain alkyl of 2 to 6 carbon atoms and at least one carbon-carbon triple bond. Exemplary alkynyl groups include ethynyl and propynyl. In some embodiments of the present invention the alkynyl group may be substituted with one or more substituents.

"Alkoxy" as used herein means an alkyl-O group in which the alkyl group is as previously described. Exemplary alkoxy groups include methoxy, ethoxy, n-propoxy, i-propoxy, n-butoxy, and t-butoxy.

"Aryl" as used herein means mono or bicyclic aromatic ring having from 6 to 10 carbon atoms. Monocyclic rings preferably have 6 members and bicyclic rings preferably have 8, 9 or 10 membered ring structures. Exemplary aryl groups include phenyl and naphthyl In some preferred embodiments aryl is phenyl, 1-naphthyl or 2-naphthyl. In still more preferred embodiments aryl is phenyl. The aryl group may be substituted with one or more substituents. Substituted aryl groups preferably have one to three substituents.

"Cycloalkyl" as used herein means a monocyclic alkyl group having from 3 to 8 carbon atoms. In some preferred embodiments cycloalkyl may be substituted with from 1 to 3 substituents.

"Heterocycloalkyl" as used herein means a monocyclic alkyl group having from 3 to 8 members containing one or more, and preferably one or two, heteroatoms selected from N and O. Exemplary heterocycloalkyl groups include piperidinyl, piperazinyl and morpholino. In some embodiments heterocycloalkyl groups may be substituted with from 1 to 3 substituents.

Halogen, as used herein means fluorine, chlorine, iodine and bromine.

"Heteroaryl" means 5 to 10 membered mono or bicyclic aromatic ring having from 1 to 3 heteroatoms selected from N, O and S. Monocyclic rings preferably have 5 or 6 members and bicyclic rings preferably have 8, 9 or 10 membered ring structures. Exemplary heteroaryls include pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl and benzodioxanyl. Preferred heteroaryl groups include thienyl, pyridyl, and furyl. More preferred are heteroaryl groups including 2-thienyl, 3-thienyl, 2-pyridyl, 3-pyridyl, 4-pyridyl, 2-furyl, and 3-furyl. The heteroaryl group may be substituted with one or more substituents.

Suitable substituents, unless otherwise noted, include halogen, alkyl, hydroxy, alkoxy, amino, amido, nitro, alkylamino, alkylamido, perhaloalkyl, carboxyalkyl, carboxy, carbamide, dialkylamino and aryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl is an alkyl-cycloalkyl group in which alkyl and cycloalkyl are as previously described.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. The individual isomers can be prepared directly or by asymmetric or stereospecific synthesis or by conventional separation of optical isomers from the racemic mixture.

Compounds of the present invention may be prepared by those skilled in the art of organic synthesis employing conventional methods which utilize readily available reagents and starting materials.

The compounds A and intermediate 4-(halo-2-methoxy-phenyl)-piperidines F or 4-(halo-2-methoxy-phenyl)-1,2,5,6-tetrahydropyridines H of the present invention can be prepared by conventional methods by those skilled in the organic synthesis. For example, in Scheme I, metal-halogen exchange of an appropriately substituted aryl halide B with a base, such as butyllithium, forms a carboanion, and treatment of the resulting mixture with an N-protected-4-piperidone C affords a tertiary alcohol D. An example of the nitrogen protecting group Rx of the 4-piperidone C is benzyl, which can be removed by hydrogenation of D to afford amine G. Dehydration of G with an acid, such as sulfuric acid can provide the desired 4-(halo-2-methoxy-phenyl)-1,2,5,6-tetrahydropyridine H. Dehydration of the tertiary alcohol D, removal of the nitroen protecting group, Rx and hydrogenation of the double bond can afford 4-(halo-2-methoxy-phenyl)-piperidine F.

The des-halo intermediates 4-(2-methoxyphenyl)-piperidine F (X=H) and 1,2,3,6-tetra hydro-4-(2-methoxyphenyl)-pyridine H (X=H) are both known compounds and may be prepared by the following literature procedures: Van Wijngaarden Ineke et al, J. Med. Chem., (1988), 31(10), 1934–1940. Perregaard Jens et al., J. Med. Chem., (1995), 38(11), 1998–2008. Modica Maria et al., J. Med. Chem., (1997), 40(4), 574–585. Solyom Sandor et al., Heterocycles, (1995), 41(6), 1139–1168.

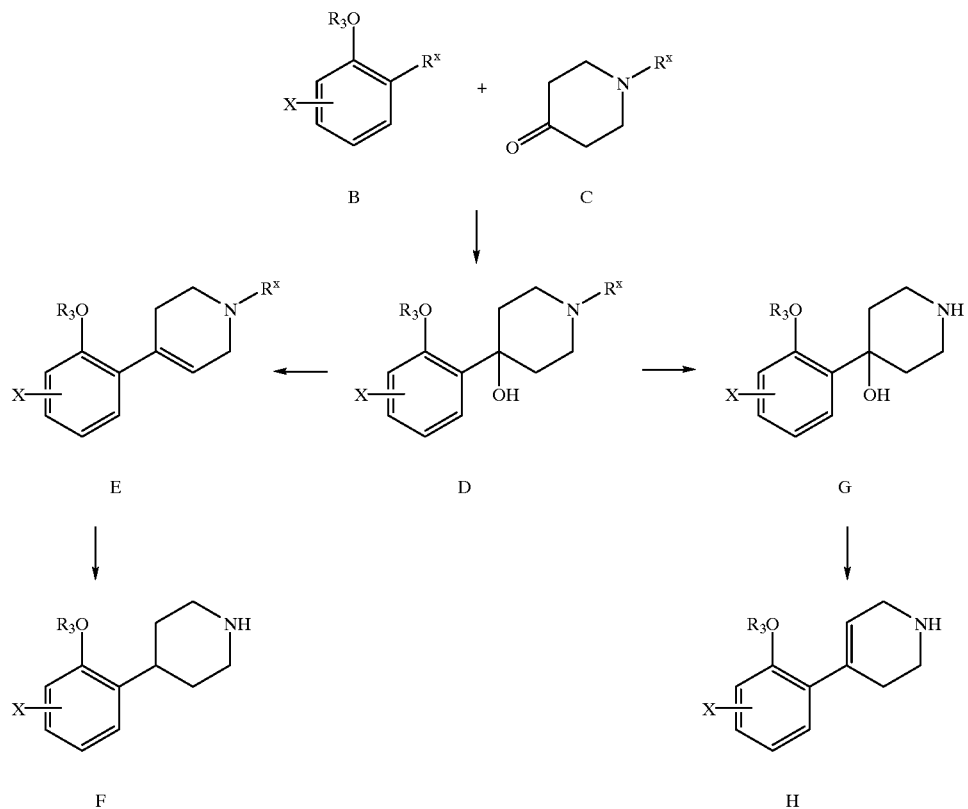

Scheme I

Coupling of 4-(X-2-methoxy-phenyl)-piperidine F (X is H or halogen) or 4-(X-2-methoxy-phenyl)-1,2,5,6-tetrahydropyridine H (X is H or halogen) with an N-protected-N-alkyl aminoacid (I) in the presence of activating reagents, such as 1-(3-dimethylaminopropyl)-3- ethylcarbodiimide hydrochloride (DAEC), 1-hydroxybenzo-triazole hydrate (HOBT), 4-methylmorpholine (NMM) forms amide J (Scheme II). The protecting group R is of the urethane type, preferably tert-butyloxycarbonyl which may be removed by the action of an acid. After deprotection, the amide may be reduced to an amine M with a reducing reagent such as lithium aluminum hydride (LAH) or diborane, and subsequently acylated to afford the urea A.

minutes, and then warmed to room temperature. The reaction was quenched by dropwise addition of saturated $NH_4Cl$ solution. The mixture was then transferred to a separatory funnel, the layers were separated and the aqueous was extracted three times with EtOAc. The combined organic phase was dried over $Na_2SO_4$, filtered and concentrated. Flash chromatography (elution with 7:3 EtOAc-hexanes) afforded 5.27 g (68%) of 1-benzyl-4-(5-fluoro-2-methoxy-phenyl)-4-hydroxypiperidine as a yellow oil.

Scheme II

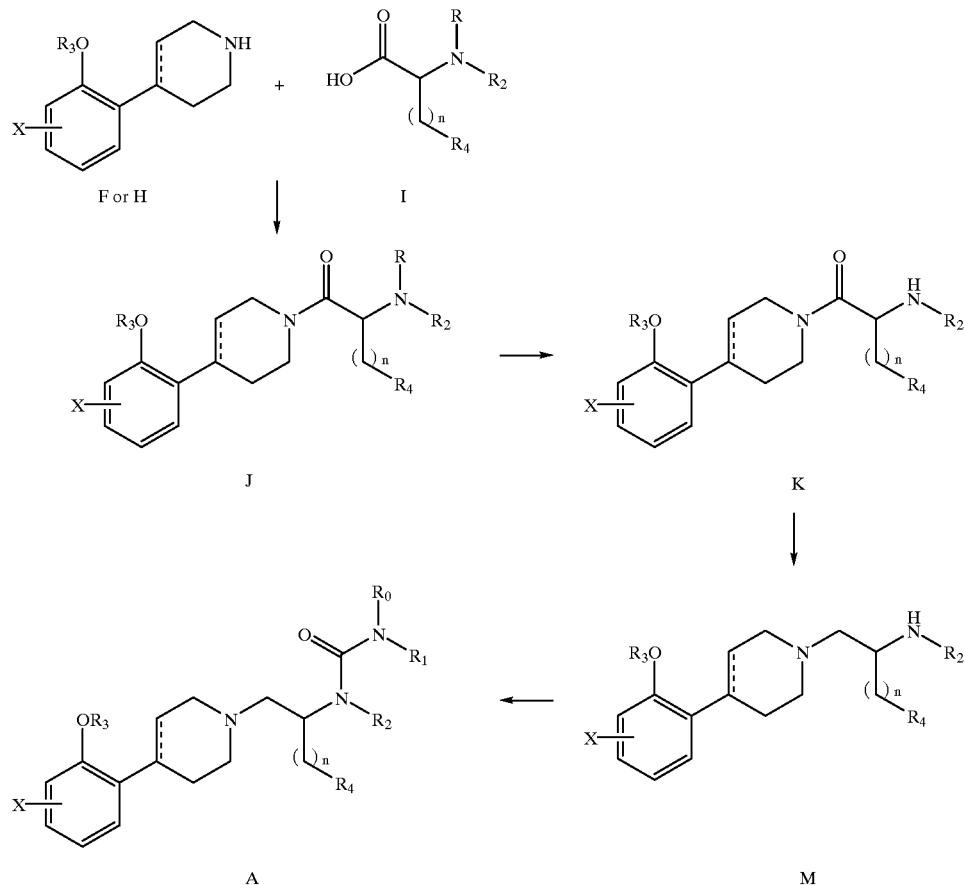

The following non-limiting specific examples are included to illustrate the synthetic procedures used for preparing compounds of the formula A. In these examples, all chemicals and intermediates are either commercially available or can be prepared by standard procedures found in the literature or are known to those skilled in the art of organic synthesis.

INTERMEDIATE 1

1-Benzyl-4-(5-fluoro-2-methoxy-phenyl)-4-hydroxypiperidine

To a solution of 9.8 mL (24 mmole) butyllithium (2.5M solution in hexane) in diethylether (20 mL) under $N_2$ at −78° C. was slowly added 2-bromo-5-fluoroanisole (5.0 g, 24 mmole) in diethylether (5 mL). The mixture was allowed to warm up to −50° C. At this point, 1-benzyl-4-piperidone (4.62 g, 24.4 mmole) in diethylether (3 mL) was added. The resulting mixture was allowed to stirred at −50° C. for 30

INTERMEDIATE 2

1-Benzyl-4-(5-fluoro-2-methoxy-phenyl)-1,2,5,6-tetrahydropyridine

To a solution of 1-benzyl-4-(5-fluoro-2-methoxy-phenyl)-4-hydroxypiperidine (1.01 g, 3.20 mmole) (Intermediate 1) in acetic acid (40 mL) at room temperature was added 2 drops of concentrated sulfuric acid. The resulting solution was heated to reflux, and the mixture stirred for 2 days. The mixture was cooled to room temperature and diluted with EtOAc (100 mL) and water (100 mL). The solution was basified with 50% NaOH solution until pH=10. The layers were separated and the organics washed with brine. The combined aqueous layers were extracted three times with EtOAc (50 mL). The combined organic layers were dried over $Na_2SO_4$ and concentrated. Flash chromatography (elution with 1:1 EtOAc-hexane) to give 0.62 g (65%) of 1-benzyl-4-(5-fluoro-2-methoxy-phenyl)-1,2,5,6-tetrahydropyridine as a yellow oil.

INTERMEDIATE 3

1-Formyl-4-(5-fluoro-2-methoxy-phenyl)-piperidine

10% Palladium on carbon (0.62 g) was added to a methanolic solution (20 mL) of 1-benzyl-4-(5-fluoro-2-methoxy-phenyl)-1,2,5,6-tetrahydropyridine (0.62 g, 2.1 mmole) (Intermediate 2). The solution was purged with $N_2$ for 5 minutes followed by dropwise addition of formic acid (2 mL, 88%) and the resulting mixture was stirred at room temperature for two days. The mixture was filtered through celite, and concentrated to afford 0.44 g (90%) of 1-formyl-4-(5-fluoro-2-methoxy-phenyl)-piperidine as a colorless oil.

Elemental Analysis for: $C_{13}H_{16}FNO_2 \cdot 0.09(C_3H_7NO)$; Calculated: C, 65.81; H, 6.80; N, 5.90; Found: C, 65.36; H, 6.87; N, 6.26.

INTERMEDIATE 4

4-(5-Fluoro-2-methoxy-phenyl)-piperidine

The crude product of 1-formyl-4-(5-fluoro-2-methoxy-phenyl)-piperidine (0.80 g, 3.4 mmole) (Intermediate 3) was dissolved in HCl (16 mL, 0.5 N) and MeOH (5 mL), and the mixture was brought to reflux for 16 hours. The mixture was cooled to room temperature and basified with NaOH (2.5 N), and extracted with EtOAc (3×25 mL) to give 4-(5-fluoro-2-methoxy-phenyl)-piperidine which was used directly without further purification.

INTERMEDIATE 5

(R)-{1-Benzyl-2-[4-(5-fluoro-2-methoxy-phenyl)-piperidin-1-yl]-2-oxo-ethyl}-methyl-carbamic acid tert-butyl ester The above product of 4-(5-fluoro-2-methoxy-phenyl)-piperidine (Intermediate 4) was dissolved in N,N-dimethylformamide (10 mL) at 0° C. To the resulting solution, 0.70 g (2.5 mmole) of 2-[N-methyl-N-(tert-butoxycarbonyl)-amino]-3-phenyl-propionic acid in a minimal amount of DMF was added, followed by 1-(3-dimethylaminopropyl)-3-ethylcarbodiimide hydrochloride (DAEC) (0.48 g, 2.5 mmole), 1-hydroxybenzotriazole hydrate (HOBT) (0.41 g, 2.5 mmole) and 4-methylmorpholine (NMM) (0.37 mL, 3.4 mmole) and the mixture was stirred overnight (the reaction temperature was slowly allowed to warm up to room temperature). The reaction mixture was diluted with water (50 mL) and EtOAc (50 mL) and the layers separated. The aqueous layer was washed with HCl (1N), saturated $NaHCO_3$, and the combined aqueous layers were extracted three times with EtOAc. The combined organic layers were dried over $Na_2SO_4$ and concentrated. Flash chromatography, gradient elution with 1:4 EtOAc-hexane to 3:7 EtOAc-hexane to afford (R)-{1-benzyl-2-[4-(5-fluoro-2-methoxy-phenyl)-piperidin-1-yl]-2-oxo-ethyl}-methyl-carbamic acid tert-butyl ester as a yellow oil.

INTERMEDIATE 6

(2R)-1-[4-(5-Fluoro-2-methoxy-phenyl)-piperazin-1-yl]-2-methylamino-3-phenyl-propan-1-one hydrochloride The above product of (R)-{1-benzyl-2-[4-(5-fluoro-2-methoxy-phenyl)-piperidin-1-yl]-2-oxo-ethyl}-methyl-carbamic acid tert-butyl ester (Intermediate 5) was dissolved in 4M HCl/dioxane (10 mL) and the resulting solution brought to reflux. After stirring overnight, the mixture was cooled to room temperature and the solvent evaporated to provide 0.38 g (22% for three steps) of the titled product.

INTERMEDIATE 7

{(1R)-1-Benzyl-2-[4-(5-fluoro-2-methoxyphenyl)-piperidin-1-yl]-ethyl}-methyl-amine To a mixture of (2R)-1-[4-(5-fluoro-2-methoxy-phenyl)-piperazin-1-yl]-2-methylamino-3-phenyl-propan-1-one hydrochloride (0.38 g, 0.93 mmole) (Intermediate 6) in tetrahydrofuran (20 mL) at (0° C. under $N_2$ atmosphere was added triethylamine (0.14 mL, 1.0 mmol), followed by the dropwise addition of lithium aluminum hydride (1.9 mL, 1.9 mmole 1M solution in THF). After addition, the cooling bath was removed and the mixture stiited at room temperature for 2.5 hours. The reaction was quenched by slow addition of saturated $NH_4Cl$ solution and the mixture was filtered through a celite pad. The solution was concentrated to afford the titled compound as a yellow oil and was used without further purification.

INTERMEDIATE 8

4-(5-Fluoro-2-methoxy-phenyl)-4-hydroxypiperidine

In a round bottom flask at room temperature was placed with 1.95 g (6.18 mmole) 1-benzyl-4-(5-fluoro-2-methoxy-phenyl)-4-hydroxypiperidine, (Intermediate 7) dry MeOH (40 mL), and the system purged with $N_2$ for 5 min. To the solution, 1.95 g of 10% palladium on carbon was added. The system was again purged with $N_2$ for 5 minutes followed by addition of 2 mL formic acid (88%). The resulting mixture was stirred at room temperature under $N_2$ for one day. At this point, a further 2 mL of formic acid (88%) was added. The reaction was continued for 2.5 days. The mixture was filtered through celite, and concentrated to afford of 4-(5-fluoro-2-methoxy-phenyl)-4-hydroxypiperidine (0.95 g 69% yield) as a yellow oil.

INTERMEDIATE 9

4-(5-Fluoro-2-methoxy-phenyl)-1,2,5,6-tetrahydropyridine

To a solution of of 4-(5-fluoro-2-methoxy-phenyl)-4-hydroxypiperidine (0.56 g, 2.5 mmole) (Intermediate 8) in acetic acid (20 mL) at room temperature was added 2 drops of concentrated sulfuric acid and the resulting solution heated to reflux for 2 days. The reaction mixture was cooled to room temperature and diluted with EtOAc (50 mL) and water (50 mL). The solution was basified with 50% NaOH solution until PH=10, the layers separated and the organic layer was washed with brine (25 mL). The combined aqueous layers were extracted three times with EtOAc (3×25 mL), and the combined organic layers were dried over $Na_2SO_4$ and concentrated to afford 0.49 g (95% yield) of 4-(5-fluoro-2-methoxy-phenyl)-1,2,5,6-tetrahydropyridine as a yellow oil.

INTERMEDIATE 10

(R)-{1-Benzyl-2-[4-(5-fluoro-2-methoxy-phenyl)-1,2,5,6-tetrahydropyridin-1-yl]-2-oxo-ethyl}-methyl-carbamic acid tert-butyl ester The crude product of 4-(5-fluoro-2-methoxy-phenyl)-1,2,5,6-tetrahydropyridine (0.49 g, 2.4 mmole) (Intermediate 9) was dissolved in N,N-dimethylformamide (10 mL) at 0° C., and the resulting solution treated with 2-[N-methyl-N-(tert-butoxycarbonyl)-amino]-3-phenyl-propionic acid (0.73 g, 2.6 mmole) in a minimal amount of DMF, DAEC (0.50 g, 2.6 mmole), HOBT (0.42 g, 3.1 mmole) and NMM (0.40 mL, 3.6 mmole). The mixture was stirred overnight, and was diluted with water (50 mL) and EtOAc (50 mL). The layers were separated and the organic layer was washed with HCl (1N), saturated NaHCO$_3$, and the combined aqueous washings were extracted three times with EtOAc (3×25 mL). The combined organic layers were dried over Na$_2$SO$_4$ and concentrated to afford (R)-{1-benzyl-2-[4-(5-fluoro-2-methoxy-phenyl)-1,2,5,6-tetrahydropyridin-1-yl]-2-oxo-ethyl}-methyl-carbamic acid tert-butyl ester as a yellow oil.

INTERMEDIATE 11

(2R)-1-[4-(5-Fluoro-2-methoxy-phenyl)-1,2,5,6-tetrahydropyridin-1-yl]-2-methylamino-3-phenyl-propan-1-one hydrochloride The crude product of (R)-{1-benzyl-2-[4-(5-fluoro-2-methoxy-phenyl)-1,2,5,6-tetrahydropyridin-1-yl]-2-oxo-ethyl}-methyl-carbamic acid tert-butyl ester (Intermediate 10) was dissolved in 10 mL 4M HCl/dioxane solution and the resulting mixture brought to reflux. After overnight stirring, the mixture was cooled to room temperature and the solvent evaporated to provide 0.62 g (65% yield for two steps) of the titled product.

INTERMEDIATE 12

{(1R)-1-Benzyl-2-[4-(5-fluoro-2-methoxy-phenyl)-1,2,3,6-tetrahydropyridin-1-yl]-ethyl}-methyl-amine To a mixture of of (2R)-1-[4-(5-fluoro-2-methoxy-phenyl)-1,2,3,6-tetrahydropyridin-1-yl]-2-methylamino-3-phenyl-propan-1-one hydrochloride (0.41 g, 1.0 mmole) (Intermediate 11) in 20 mL of tetrahydrofuran at 0° C. under N$_2$ was added of triethylamine (0.14 mL, 1.0 mmol), followed by slow addition of 1.9 mL (1.9 mmole) lithium aluminum hydride (1M solution in THF). After addition, the cooling bath was removed and the mixture was stirred at room temperature for 2.5 hours. The reaction was quenched by the slow addition of saturated NH$_4$Cl solution and the mixture was filtered through a celite pad. The solution was concentrated to afford 0.36 g (100%) {(1R)-1-benzyl-2-[4-(5-fluoro-2-methoxy-phenyl)-1,2,5,6-tetrahydropyridin-1-yl]-ethyl)}-methyl-amine as a yellow oil which was used without further purification.

EXAMPLE 1

1-{(1R)-1-Benzyl-2-[4-(5-fluoro-2-methoxyphenyl)-piperidin-1-yl]-ethly}-1-3-cyclohexyl-1-methyl-urea Under a N$_2$ atmosphere, a solution of {(1R)-1-benzyl-2-[4-(5-fluoro-2-methoxy-phenyl)-piperidin-1-yl]-ethyl}-methyl-amine (0.12 g, 0.33 mmole, described as intermediate 7 above) and triethylamine (0.10 mL, 0.74 mmole) in dichloromethane (10 mL) was cooled to 0° C. Cyclohexyl isocyanate (0.050 rmL, 0.35 mmole) was added dropwise and the resulting mixture was stirred at 0° C. to room temperature (ice melt) overnight. The solvent was evaporated and the residue dissolved in EtOAc (25 mL) and water (25 mL). The layers were separated and the organic layer washed with water (25 mL) and brine. The combined organic washings were extracted three times with EtOAc (25 mL), then dried over Na$_2$SO$_4$, filtered and concentrated. Flash chromatography (elution with 7:3 EtOAc-hexane) to give 0.16 g (100% yield) of 1-{(1R)-1-benzyl-2-[4-(5-fluoro-2-methoxy-phenyl)-piperidin-1-yl]-ethyl}-3-cyclohexyl-1-methyl-urea. An ethanolic solution of the product was heated to gentle reflux and 1 equivalent of fumaric acid in hot ethyl alcohol solution was added to afford the fumarate salt of the titled compound as a white solid.

mp 70–80° C.; Elemental Analysis for: C$_{29}$H$_{40}$FN$_3$O$_2$.1.0C$_4$H$_4$O$_4$.1.0H$_2$O; Calculated: C, 64.37; H, 7.53; N, 6.82; Found: C, 64.28; H, 7.58; N, 6.96.

EXAMPLE 2

Morpholine-4-carboxylic acid {(1R)-1-benzyl-2-[4-(5-fluoro-2-methoxy-phenyl)-1,2,5,6-tetrahydro-4H-pyridin-1-yl]-ethyl}-methyl-amide Under a N$_2$ atmosphere, a solution of of {(1R)-1-benzyl-2-[4-(5-fluoro-2-methoxyphenyl)-1,2,5,6-tetrahydropyridin-1-yl]-ethyl}-methyl-amine (0.17 g, 0.48 mmole described as intermediate 12 above) and triethylamine (0.15 mL, 1.0 mmole) in dichloromethane (10 mL) was cooled to 0° C. 4-Morpholinecarbonyl chloride (0.06 mL, 0.51 mmole) was added and the resulting mixture was stirred at 0° C. to room temperature (ice melt) overnight. The solvent was evaporated to give a brown residue. Flash chromatography (elution with 7:3 EtOAc-hexane) gave 0.17 g (74% yield) of morpholine-4-carboxylic acid {(1R)-1-benzyl-2-[4-(5-fluoro-2-methoxy-phenyl)-1,2,5,6-tetrahydro-4H-pyridin-1-yl]-ethyl}-methyl-amide. An ethanolic solution of the product was heated to gentle reflux and 1 equivalent of fumaric acid in hot ethyl alcohol solution was added to afford the fumarate salt of the titled compound as a white solid.

mp 70–75° C.; Elemental Analysis for: C$_{27}$H$_{34}$FN$_3$O$_3$.1.0C$_4$H$_4$O$_4$.0.8H$_2$O.0.8C$_2$H$_6$O; Calculated: C, 62.05; H, 6.81; N, 6.88; Found: C, 62.12; H, 6.54; N, 6.67.

EXAMPLE 3

1-{(1R)-1-Benzyl-2-[4-(5-fluoro-2-methoxy-phenyl)-1,2,5,6-tetrahydro-4H-pyridin-1-yl]-ethyl-}-3-cyclohexyl-1-methyl-urea Under a N$_2$ atmosphere, a solution of {(1R)-1-benzyl-2-[4-(5-fluoro-2-methoxy-phenyl)-1,2,3,6-tetrahydropyridin-1-yl]-ethyl}-methyl-amine (0.17 g, 0.48 mmole, described as intermediate 12 above) and triethylamine (0.15 mL, 1.0 mmole) in dichloromethane (10 mL) was cooled to 0° C. and a solution of cyclohexyl isocyanate (0.070 mL, 0.51 mmole) was added dropwise. The resulting mixture was stirred at 0° C. to room temperature (ice melt) overnight. The solvent was evaporated and the residue dissolved in EtOAc (25 mL) and water (25 mL). The layers were separated and the organics washed with water (25 mL), brine (30 mL) and dried over Na$_2$SO$_4$. Filtration and concentration gave the crude product which was purified by flash chromatography (elution with EtOAc) to yield 0.19 g (83% yield) of 1-{(1R)-1-benzyl-2-[4-(5-fluoro-2-methoxy-phenyl)-1,2,5,6-tetrahydro-4H-pyridin-1-yl]-ethyl}-3-cyclohexyl-1-methyl-urea. An ethanolic solution of the product was heated to gentle reflux and 1 equivalent of fumaric acid in hot ethyl alcohol solution was added to afford the fumarate salt of the titled compound as a white solid.

mp 75–80° C. Elemental Analysis for: C$_{29}$H$_{38}$FN$_3$O$_2$.1.0C$_4$H$_4$O$_4$.1.0H$_2$O; Calculated: C, 64.58; H, 7.23; N, 6.85; Found: C, 64.14; H, 6.09; N, 6.65.

EXAMPLE 4

1-{(1R)-1-(Pyridin-3-ylmethyl)-2-[4-(2-methoxyphenyl)-piperidin-1-yl]-ethyl}-3-cyclohexyl-urea 4-(2-Methoxyphenyl)piperidine (1.0 g, 4.39 mmol) was added to a solution of N-Boc-3'-(3'-pyridyl)-D-alanine (1.17 g, 4.39 mmol), DEAC (0.84 g, 4.39 mmol), and HOBT (0.77 g, 1.3 eq.) in DMF (20 mL) at 0° C., followed by the addition of NMM (0.7 mL, 1.5 eq.). The mixture was stirred under nitrogen overnight at ambient temperature, then diluted with ethyl acetate (50 mL), washed with 0.1N HCl (15 mL), saturated $NaHCO_3$, $H_2O$ and finally brine. The organic phase was dried over anhydrous $Na_2SO_4$, filtered and concentrated under vacuum to yield crude product (100%). This was stirred in 4.0M HCl/dioxane (40 mL) overnight and concentrated to afford the amine hydrochloride salt, from which the free base was liberated by treatment with a saturated $NaHCO_3$ solution. The amide was dissolved in THF (50 mL) and the resulting solution treated with the dropwise addition of $BH_3$.THF (10 equivalents) and the mixture refluxed for 16 hours. After cooling, the reaction was terminated by the addition of 2N HCl, and after stirring for eight hours the mixture was concentrated in vacuo. The aqueous solution was made basic and the product extracted into EtOAc (3×25 mL), the combined organics were washed with water (50 mL), brine, separated and dried over anhydrous $Na_2SO_4$. Filtration and concentration under vacuum gave the required product (100% yield). Under a $N_2$ atmosphere, a solution of {(1R)-1-(3-pyridyl-methyl)-2-[4-(5-fluoro-2-methoxyphenyl)-piperidin-1-yl]-ethyl}-amine (0.13 g, 0.33 mmole), and triethylamine (0.10 mL, 0.74 mmole) in dichloromethane (10 mL) was cooled to 0° C. Cyclohexyl isocyanate (0.050 mL, 0.35 mmole) was added dropwise and the resulting mixture was stirred at 0° C. to room temperature (ice melt) overnight. The solvent was evaporated and the residue dissolved in EtOAc (25 mL) and water (25 mL). The layers were separated and the organic layer washed with water (25 mL) and brine. The combined organic washings were extracted three times with EtOAc (25 mL), then dried over $Na_2SO_4$, filtered and concentrated. Flash chromatography (elution with 7:3 EtOAc-hexane) to give 0.16 g (100% yield) of 1-{(1R)-1-(pyridin-3-yl-methyl)-2-[4-(5-fluoro-2-methoxy-phenyl)-piperidin-1-yl]-ethyl}-3-cyclohexyl-urea. An ethanolic solution of the product was heated to gentle reflux and 1 equivalent of fumaric acid in hot ethyl alcohol solution was added to afford the fumarate salt of the titled compound as a white solid.

Elemental Analysis for: $C_{27}H_{38}FN_4O_2.1.0C_4H_4O_4$; Calculated: C, 65.70; H, 7.47; N, 9.89; Found: C, 65.67; H, 7.40; N, 9.80.

Compounds of the present invention bind with very high affinity to the 5-HT1A receptor and consequently, they are useful for the treatment of primary disorders of the central nervous system such as depression, anxiety and panic, as well as secondary attending problems such as sleep disorders and sexual dysfunction. Compounds of the present invention are also useful for other disorders of the central nervous system including alcohol and drug addiction, obesity and migraine. Cognition enhancement may be achieved by use of compounds of the present invention and neurodegenerative diseases such as Alzheimer's disease and Parkinson's disease may be treated.

5-HT1A Receptor Binding Assay

High affinity for the serotonin $5-HT_{1A}$ receptor was established by testing a compound's ability to displace [$^3$H] 8-OH-DPAT binding in CHO cells stably transfected with human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5-HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1,0.1, and 0.01 mM, and Ki values are determined for the active compounds.

5-HT1A Receptor Intrinsic Activity Assay

The intrinsic activity of compounds of the present invention was established by testing the claimed compounds ability to reverse the stimulation of cyclic adenosinemonophosphate (cAMP) in CHO cells stably transfected with the human 5-HT1A receptor.

Stably transfected CHO cells were grown in DMEM containing 10% heat inactivated FBS and non-essential amino acids. The cells are plated at a density of ?×10$^6$ cells per well in a 24 well plate and incubated for 2 days in a $CO_2$ incubator. On the second day, the media is replaced with 0.5 mL treatment buffer (DMEM +25 mM HEPES, 5 mM theophylline, 10 μM pargyline) and incubated for 10 minutes at 37° C. Wells are treated with forskolin (1 μM final concentration) followed immediately by the test compound (0.1 and 1 μM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. $EC_{50}$ values are determined for the active test compounds. Compounds shown to have no agonist activities (Emax=0%) are further analyzed for their ability to reverse agonist induced activity. In separate experiments, 6 concentrations of antagonist are preincubated for 20 minutes prior to the addition of agonist and forskolin. Cells are harvested as described above. The cAMP kit is supplied by Amershan and the RIA is performed as per kit instructions, and calculations of $IC_{50}$ performed by GraphPad Prism.

| Compound | 5-HT1A binding Ki (nM) | cAMP Emax | $IC_{50}$ (nM) |
|---|---|---|---|
| Example 1 | 3.5 | 0% | 46.9 |
| Example 2 | 26.6 | 0% | |
| Example 3 | 3.5 | 0% | 12.6 |

Hence, compounds of the present invention exhibit high affinity for the 5HT1A receptor subtype and exhibit intrinsic activity as evidenced by their ability to reverse stimulation of cyclic adenosinemonophosphate (cAMP). Accordingly, compounds of the present invention are useful for treatment of disorders of the central nervous system and may be administered to a patient suffering from one or more of said disorders. Treatment, as used herein, refers to alleviation or amelioration of symptoms of a particular disorder in a patient. In addition, compounds of the present invention may be administered as part of a treatment regime that includes other agents which act on the central nervous system. In some preferred embodiments, compounds of the present invention are part of a combination therapy including a serotonin reuptake inhibitor. Serotonin reuptake inhibitors useful in combination therapies of the present invention fluoxetine, fluvoxamine, paroxetine, sertraline and venlafaxine. Said agents may be administered at the same time, where they may be combined into a single dosage form, or at a different time, as compounds of the present invention, while still being part of the regime of the combination therapy.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid canrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. (glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of Formula A and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1–100 mg/Kg for parenteral application, preferably 0.5–50 mg/Kg.

What is claimed is:

1. A compound of the Formula (A),

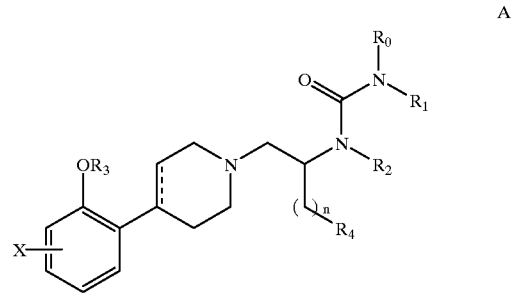

in which:

R0 and R1 are independently hydrogen, alkyl, cycloalkyl, heterocycloalkyl alkylcycoalkylm alkylheterocyclalkyl, aryl or heteroaryl, or taken together R0 and R1 form a heterocycloalkyl, provided that R0 and R1 are not both hydrogen;

R2 is hydrogen, alkyl or $CH_2(R_5)$;

R3 is hydrogen or alkyl;

R4 is aryl or heteroaryl;

R5 is alkyl, alkenyl or alkynyl;

X is hydrogen, halogen, perhaloalkyl, hydroxy, alkoxy, perhaloalkoxy; n is an integer from 1 to 3; and the dotted line is an optional double bond, or a pharmaceutical salt thereof.

2. A compound of claim 1 wherein R0 and R1 taken together are cycloalkyl or heterocycloalkyl.

3. A compound of claim 1 wherein R0 and R1 are independently hydrogen or cycloalkyl.

4. A compound of claim 1 wherein X is a halogen at position 4- or 5-.

5. A compound of claim 1 wherein R0 and R1 are independently H or cyclohexyl or taken together are morpholino; X is 5-fluoro-; and R4 is phenyl.

6. A compound of claim 1 which is 1-{(1R)-1-Benzyl-2-[4-(5-fluoro-2-methoxyphenyl)-piperidin-1-yl]-ethyl}-3-cyclohexyl-1-methyl-urea, or a pharmaceutical salt thereof.

7. A compound of claim 1 which is Morpholine-4-carboxylic acid {(1R)-1-benzyl-2-[4-(5-fluoro-2-methoxy-phenyl)-1,2,5,6-tetrahydro-4H-pyridin-1-yl]-ethyl}-methyl-admide, or a pharmaceutical s alt thereof.

8. A compound of claim 1 which is 1-{(1R)-1-Benzyl-2-[4-(5-fluoro-2-methoxy-phenyl)-1,2,5,6-tetrahydro-4H-pyridin-1-yl]-ethyl}-3-cyclohexyl-1-methyl-urea, or a pharmaceutical salt thereof.

9. A compound of claim 1 which is 1-{(1R)-1-(Pyridin-3-ylmethyl)-2-[4-(2-methoxy phenyl)-piperidin-1-yl]-ethyl}-3-cyclohexyl-urea, or a pharmaceutical salt thereof.

10. A pharmaceutical composition comprising a compound of claim 1 and a pharmaceutically acceptable carrier.

11. A method of treating a patient suffering from a disorder of the central nervous system associated with the 5-hydroxytryptamine-1A receptor subtype com prising administering a therapeutically effective amount of a compound of Formnula (A),

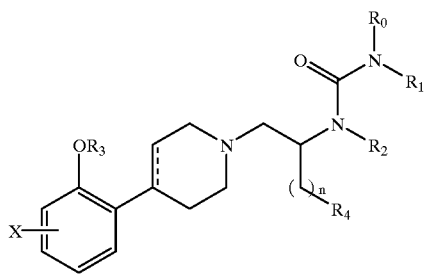

in which:
R0 and R1 are independently hydrogen, alkyl, cycloalkyl, heterocycloalkyl alkylcycloalkyl, alkylheterocycloalkyl, aryl or heteroaryl, or taken together R0 and R1 form a heterocycloalkyl, provided that R0 and R1 are not both hydrogeon;
R2 is hydrogen, alkyl or $CH_2(R_5)$;
R3 is hydrogen or alkyl;
R4 is aryl or heteroaryl;
R5 is alky, alkenyl or alkynyl;
X is hydrogen, halogen, perhaloalkyl, hydroxy, alkoxy, perhaloalkoxy; n is an integer from 1 to 3; and the dotted line is an optional double bond, or a pharmaceutical salt thereof.

12. The method of claim 11 wherein the disorder is depression, anxiety or panic.

13. The method of claim 11 wherein the disorder is a sleep disorder or sexual dysfunction.

14. The method of claim 11 wherein the disorder is drug or alcohol addiction.

15. The method of claim 11 wherein the disorder is a cognitive disorder.

16. The method of claim 11 wherein the disorder is a neurodegenerative disease.

17. The method of claim 16 wherein the neurodegenerative disease is Parkinson's disease or Alzheimer's disease.

18. The method of claim 11 wherein the disorder is migraine.

19. The method of claim 11 wherein the disorder is obesity.

20. The method of claim 11 further comprising administration of a serotonin reuptake inhibitor.

21. The method of claim 20 wherein the serotonin reuptake inhibitor is selected from the group consising of fluoxetine, fluvoxamine, paroxetine, sertraline and venlafaxine.

* * * * *